United States Patent [19]

Warren et al.

[11] 4,127,033
[45] Nov. 28, 1978

[54] ULTRASONIC SCANNER SYSTEM FOR CAST EXPLOSIVE BILLETS

[75] Inventors: Jeffrey M. Warren, Fredericksburg, Va.; Gerald V. Blessing, Camp Springs, Md.

[73] Assignee: The United States of America as represented by the Secretary of the Navy, Washington, D.C.

[21] Appl. No.: 716,734

[22] Filed: Aug. 23, 1976

[51] Int. Cl.² ............................................. G01N 29/04
[52] U.S. Cl. ........................................ 73/622; 73/625
[58] Field of Search .............. 73/67.5 R, 67.7, 67.8 R, 73/67.8 S, 67.6, 618, 622, 624, 625, 633, 640, 641

[56] References Cited

U.S. PATENT DOCUMENTS

| 2,758,706 | 8/1956 | Quinlan | 73/618 |
| 3,529,466 | 9/1970 | Pryor et al. | 73/622 |
| 3,575,043 | 4/1971 | Allen et al. | 73/635 |
| 3,981,184 | 9/1976 | Matay | 73/622 |

*Primary Examiner*—Stephen A. Kreitman

[57] ABSTRACT

An apparatus for ultrasonic inspection of polyethylene-jacketed, cast explosive billets including an immersion tank and a roller system for axially rotating the billet while immersed in the coupling fluid. A drive mechanism traverses a pair of laterally opposed transducers axially of the rotating billet for through-transmission inspection of the majority of the billet. A second drive mechanism sweeps a third transducer through a 90° arc for pulse-echo inspection of the hemispherical base of the billet.

1 Claim, 3 Drawing Figures

ULTRASONIC SCANNER SYSTEM FOR CAST EXPLOSIVE BILLETS

BACKGROUND OF THE INVENTION

This invention relates generally to ultrasonic inspection apparatus and more particularly to an ultrasonic apparatus for detecting small voids or air pockets inadvertently formed in cast explosive billets used in two piece shells.

For a number of years the U.S. Navy has had evidence that a dangerous situation may result from the presence of air pockets at certain locations in its projectiles. Specifically, air cavities within the explosive and air gaps between the explosive and aft end of a projectile are considered problems. Theoretical calculations show that the tremendous setback forces experienced by the explosive in a gun launch situation may generate sufficiently high temperatures in the vicinity of the cavities due to adiabatic heating to cause a premature initiation of the explosive. Recent firing test results with 5 inches/54 projectiles indicate that possibly a combination involving both an explosive base-to-shell air gap and the presence of voids within the explosive volume is a critical situation in gun launch.

These facts demonstrate a need for the nondestructive inspection of the Navy's cast explosives. Traditionally, the billets have been X-rayed for the presence of air cavities inadvertently formed by gases trapped in the highly viscous explosive mixture during the casting process. However, a non-destructive inspection technique that would be less operator dependent and potentially more reliable or less costly, and would also provide for the real-time detection of flaws is preferred. An investigation of the ultrasonic technique originated with these goals in mind.

SUMMARY OF THE INVENTION

The present invention provides a non-destructive test apparatus for detecting small voids in cast explosive billets. A pair of ultrasonic transducers, operating in the through-transmission (T-T) mode, traverse a rotating explosive billet on opposite sides thereof to inspect the substantially cylindrical portion of the billet. A third ultrasonic transducer, operating in the pulse-echo (P-E) mode, traverse a 90° arc to inspect the hemispherical base of the billet where refraction problems preclude through-transmission inspection. Appropriate electronic apparatus is used to provide oscilloscope traces representative of the acoustic signals, and a strip chart recorder to provide a permanent record.

DESCRIPTION OF THE PREFERRED EMBODIMENT

Figure 1:
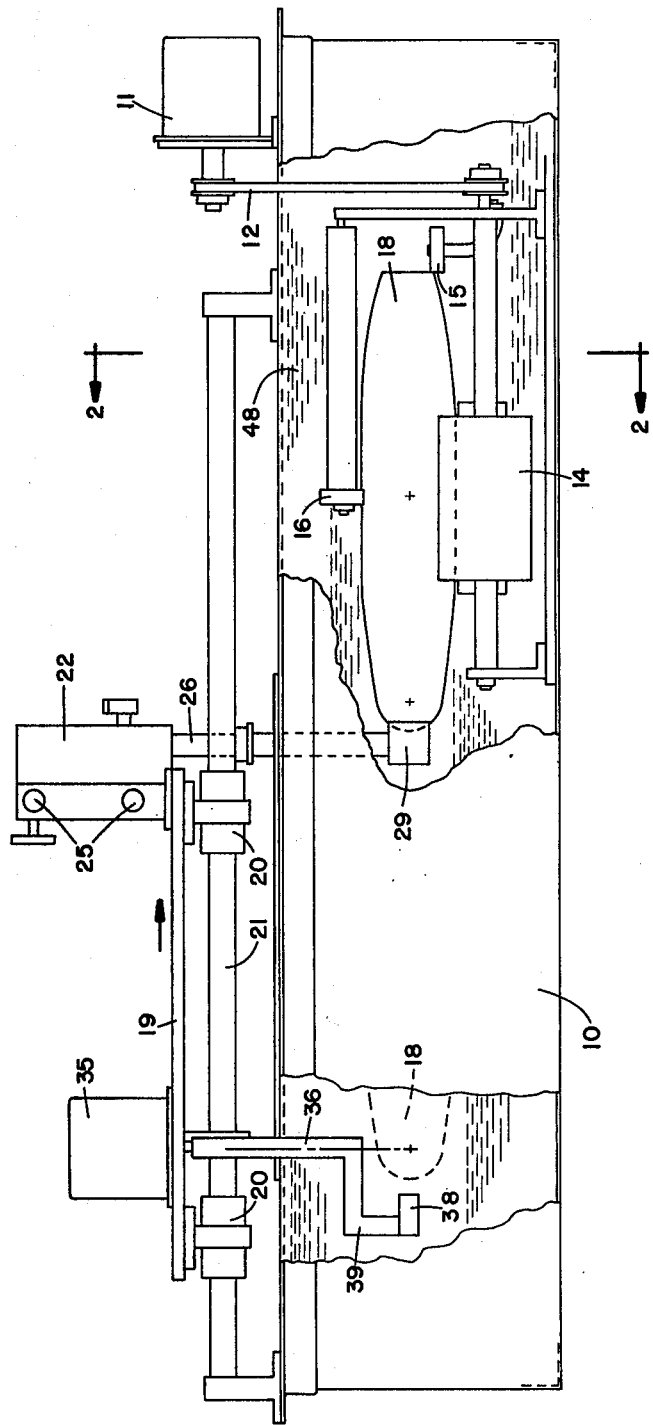
FIG. 1 is an elevation view, partially in section, illustrating the mechanism for rotating the billets and traversing the transducers relative to the billets.
Figure 2:
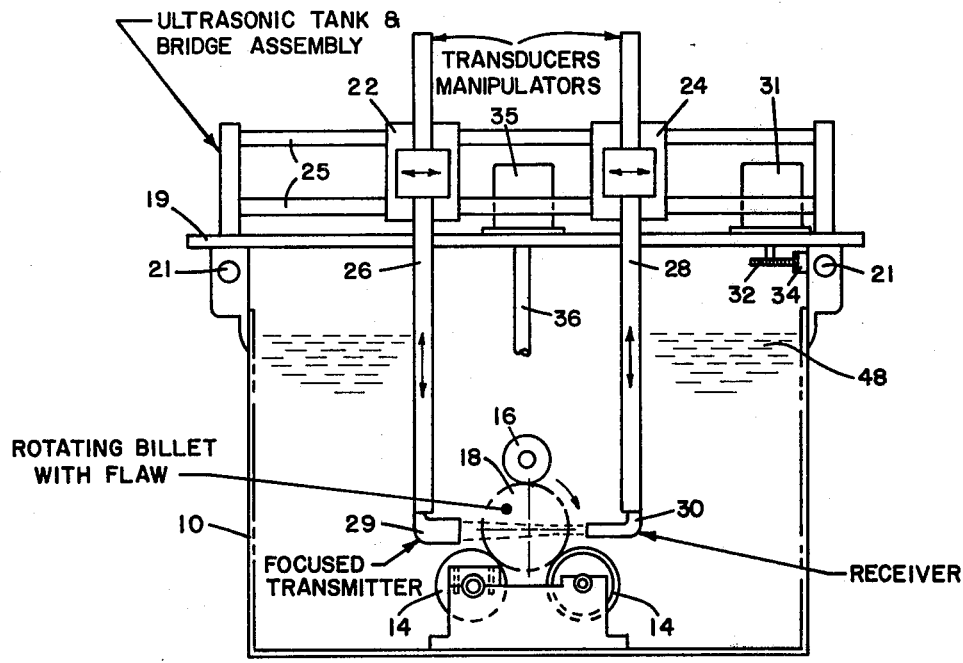
FIG. 2 is a sectional view, taken along the line 2—2 of FIG. 1, and illustrates the billet rotating mechanism and through-transmission transducer configuration.

Referring now to the drawings, wherein like numerals of reference designate like parts throughout the several views, and more particularly to FIGS. 1 and 2, there can be seen a tank 10, of stainless steel or other corrosive resistant material, for containing water or other suitable ultrasonic coupling liquid. A drive motor 11 and belt 12 are provided for rotating two support rollers 14 mounted on the bottom of the tank 10. The drive mechanism is also provided with an idler roller 15 and a pivotally mounted weighted roller 16 for retaining an explosive billet 18 in position during operation.

A plate 19 is mounted for reciprocation longitudinally of the tank 10 by means of linear bearings 20 riding on rods 21 fixed to the sides of the tank. A pair of blocks 22 and 24 (FIG. 2) are slidably mounted on rods 25 for movement laterally with respect to the tank 10. The blocks 22 and 24 carry transducer manipulators 26 and 28, respectively, which are mounted for vertical adjustment by means of appropriate mechanism (not shown). A focused ultrasonic transmitter 29 is mounted on the lower extremity of the manipulator 26 and an ultrasonic receiver 30 is similarly mounted on the manipulator 28.

A stepping motor 31 (FIG. 2) is provided for translating the plate 19 along the guides 21 by means of a pinion 32 on the motor shaft engaging a rack 34 secured to the tank 10. A base inspection motor 35 is mounted on the plate 19 and centrally located with respect to the longitudinal axis of the tank 10. A vertically adjustably transducer support 36 is mounted on the motor 35 and carries an ultrasonic transmit and receive transducer 38 on the lower extremity thereof. The support 36 is provided with an offset portion 39 so that the axis of the motor 35 may be positioned to intersect the center of curvature of the hemispherical base of the billet 18.

Figure 3:
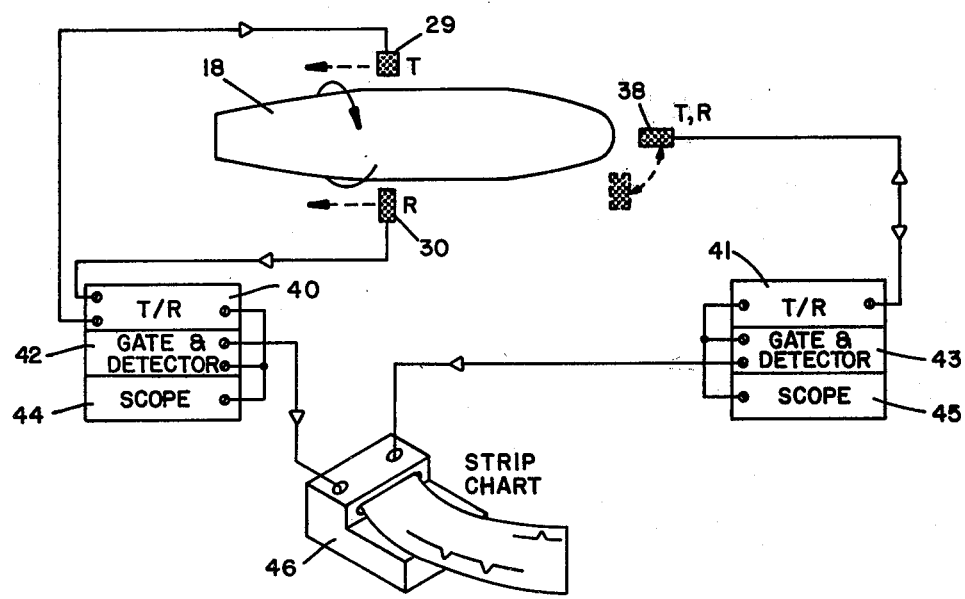
FIG. 3 is a schematic representation of the inspection system of the present invention.

Referring now to FIG. 3, there can be seen a schematic representation of the system of the present invention. Separate transmitter-receivers 40 and 41; gates and detectors 42 and 43; and display scopes 44 and 45 are used for through-transmission (T-T) and pulse-echo (P-E), respectively. The respective outputs are recorded on a dual-channel, striprecorder 46. A void detected by T-T in the body of the billet 18 is registered as a negative excursion of the pen superimposed on the baseline curve which itself reflects the billet curvature. A void detected by P-E in the hemispherical base of the billet is registered as a positive excursion of the pen superimposed on a flat baseline. The P-E baseline trace, instead of being flat, may also be displayed as a relatively constant background noise level caused by an increased receiver gain to provide a greater sensitivity for void detection.

Operation

In order that a better understanding of the invention might be had, its mode of operation will now be described. An explosive billet 18 is placed in the tank 10 on the rollers 14 and abutting the idler 15. The gravity roller 16 is then rotated into the position shown in FIG. 1 and the tank filled with an ultrasonic coupling liquid 48 to a point where it covers the billet by at least ½ inch. The liquid 48 may be water, sugar water, ethylene glycol, glycerine, ethylene glycol mixed with water, or any other suitable liquid which provides a good acoustic impedance match with the polyethylene beaker.

Power is applied to the transducers 29 and 30 and the drive motor 31 is energized to begin movement of the plate 19 to the right as viewed in FIG. 1. Simultaneously, the motor 11 is started to effect rotation of the billet 18 about its longitudinal axis. As the transducers 29 and 30 traverse the billet 18 they scan a helical or spiral path along the billet. In order to determine the optimum operating frequency for acoustic flaw detection, it is necessary to measure the frequency dependence of the ultrasonic attenuation in the explosive. A compromise must be made between operating at a higher frequency where flaw resolution and detection are at a maximum, and operating at a lower frequency when the electronic signal to noise ratio is greater and, therefore, the acoustic signal is more easily interpreted and recorded. The choice of operating frequency depends in turn on the corresponding wavelengths of the ultrasonic energy in the material. The wavelength should be on the order of the minimum size void to be detected. The explosive used in testing the invention was PBXN-106 in which the acoustic velocity is 0.20 centimeters per microsecond. Consequently, a frequency of 1MHz is a nominal value for the transducers 29 and 30 for detecting 0.25 cm (0.10 inches) voids with somewhat lower frequencies still providing useful results. Any flaws detected by the transducers 29 and 30 are registered on the scope 44 and recorded by the strip chart recorder 46.

When the transducers 29 and 30 have completed their traverse of the substantially cylindrical portion of the billet 18, the drive motor 31 is automatically stopped by means not shown and simultaneously the base inspection motor is energized. At this time the axis of the motor 35 is positioned to intersect the center of curvature of the hemispherical base of the billet 18. Consequently, rotation of the support 36 will traverse the transducer 38 through an arc about the hemispherical base of the billet and at a constant distance therefrom. To illustrate this relationship, a portion of the billet 18 is shown in phantom in FIG. 1. although it should be realized that this geometric relationship is not obtained until the plate 19 has traversed to its extreme rightward position. Any flaws detected by the transducer 38 are displayed on the scope 45 and recorded by the strip chart recorder 46. When the base inspection is concluded the motor 35 is stopped and the drive motor 31 reversed to return the plate 19 to the position shown in FIG. 1. The inspected billet 18 may then be removed and replaced by the next billet to be inspected and the sequence described above may then be again initiated.

Obviously many modifications and variations of the present invention are possible in the light of the above teachings. It is therefore to be understood that within the scope of the appended claims the invention may be practiced otherwise than as specifically described.

What is claimed is:

1. An apparatus for nondestructive inspection of and void detection in substantially cylindrical polyethylene-jacketed cast explosive billets having a hemispherical base comprising:

a tank for holding an ultrasonic coupling liquid;

means fixed to the bottom of said tank for supporting the explosive billet and for rotating the billet about its longitudinal axis;

a supporting plate mounted for reciprocation along the top of said tank;

a pair of ultrasonic transducers adjustably mounted on and depending from said supporting plate and operable in the through-transmission mode for inspecting the substantially cylindrical portion of the billet;

a third ultrasonic transducer adjustably mounted on and depending from said supporting plate and operable in the pulse-echo mode for inspecting the hemispherical base of the explosive billet;

means for driving said billet rotating means and for traversing said supporting plate whereby said first pair of transducers will track along the substantially cylindrical portion of said billet and said third transducer will first be moved into proximity with the hemispherical base of the billet and then moved through an arcuate path at a constant distance from the hemispherical base of the billet for inspection thereof; and means for displaying and recording the existence and location of voids within the explosive billet.

* * * * *